United States Patent
Kowalczyk et al.

(10) Patent No.: US 9,895,316 B2
(45) Date of Patent: Feb. 20, 2018

(54) ISOMALT-CONTAINING TABLETS AND METHODS FOR THE PRODUCTION THEREOF

(75) Inventors: Jörg Kowalczyk, Eisenberg-Steinborn (DE); Oliver Luhn, Birkenheide (DE)

(73) Assignee: SUDZUCKER AKTIENGESELLSCHAFT MANNHEIM/OCHSENFURT, Mannheim (DE)

( * ) Notice: Subject to any disclaimer, the term of this patent is extended or adjusted under 35 U.S.C. 154(b) by 500 days.

(21) Appl. No.: 12/867,860

(22) PCT Filed: Feb. 4, 2009

(86) PCT No.: PCT/EP2009/000712
§ 371 (c)(1),
(2), (4) Date: Aug. 16, 2010

(87) PCT Pub. No.: WO2009/109266
PCT Pub. Date: Sep. 11, 2009

(65) Prior Publication Data
US 2010/0317746 A1     Dec. 16, 2010

(30) Foreign Application Priority Data
Mar. 1, 2008   (DE) ........................ 10 2008 012 015

(51) Int. Cl.
*A61K 9/20*   (2006.01)
*A61K 9/00*   (2006.01)
*A61K 9/14*   (2006.01)

(52) U.S. Cl.
CPC .......... *A61K 9/2018* (2013.01); *A61K 9/0056* (2013.01); *A61K 9/145* (2013.01)

(58) Field of Classification Search
CPC .... A61K 9/2018; A61K 9/0056; A61K 47/26; A61K 9/145
See application file for complete search history.

(56) References Cited

U.S. PATENT DOCUMENTS

| 5,478,593 | A | * | 12/1995 | Serpelloni et al. | .......... 427/2.14 |
| 5,785,957 | A | * | 7/1998 | Losee | ................ A61K 8/22 |
| | | | | | 424/49 |
| 6,224,904 | B1 | | 5/2001 | Rapp et al. | |
| 6,849,286 | B1 | | 2/2005 | Bayerköhler et al. | |
| 6,890,559 | B1 | | 5/2005 | Bayerköhler et al. | |

(Continued)

FOREIGN PATENT DOCUMENTS

DE   19639343 A1   4/1998
DE   19943491 A1   3/2001

(Continued)

OTHER PUBLICATIONS

English Translation of the International Preliminary Report on Patentability (Chapter I), IB, Geneva, dated Nov. 9, 2010, incorporating the English Translation of the Written Opinion of the ISA, ISA/EP.

(Continued)

*Primary Examiner* — Lakshmi S Channavajjala
(74) *Attorney, Agent, or Firm* — Stephen T. Olson; Harness, Dickey & Pierce, P.L.C.

(57) ABSTRACT

The invention relates to improved isomalt-containing tablets and to methods for the production thereof.

21 Claims, 3 Drawing Sheets

(56) References Cited

U.S. PATENT DOCUMENTS

Figure 1:
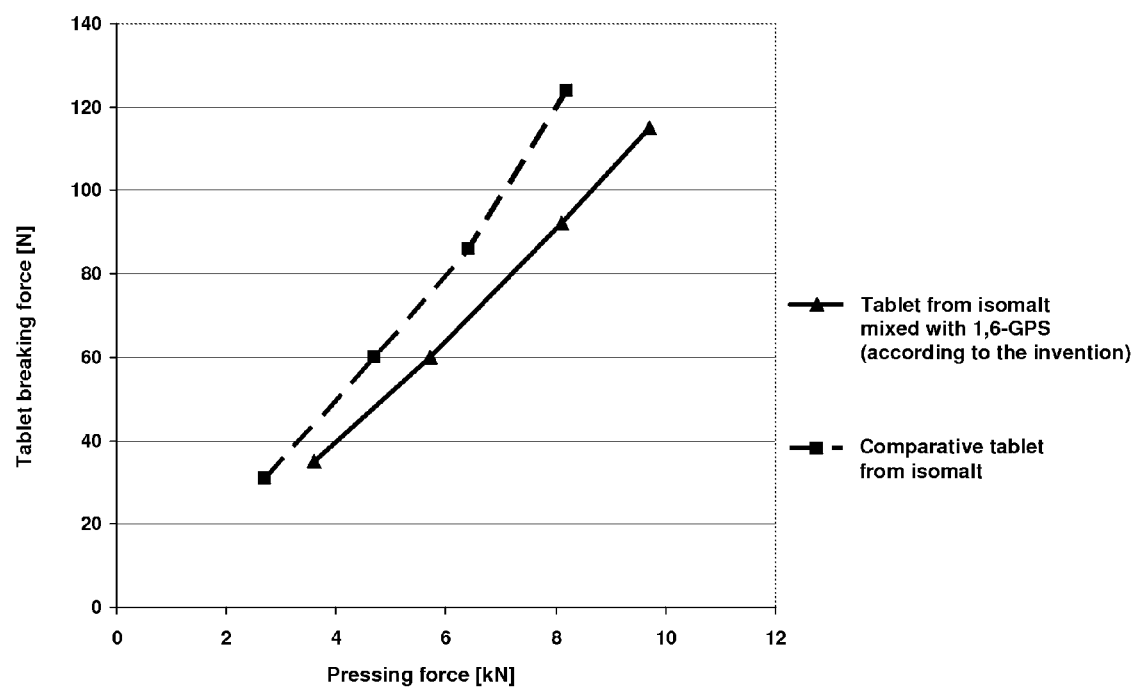

| | | | |
|---|---|---|---|
| 8,846,101 B2 * | 9/2014 | Piene | ............. A23L 33/16 424/490 |
| 2003/0162726 A1 | 8/2003 | Rapp et al. | |

FOREIGN PATENT DOCUMENTS

| | | | | |
|---|---|---|---|---|
| DE | 19943496 C1 | | 5/2001 | |
| EP | 1013175 | | 6/2000 | |
| WO | WO 99/55342 A1 | | 11/1999 | |
| WO | WO 02/076211 A1 | | 10/2002 | |
| WO | WO2007/065441 | * | 6/2007 | ............. A23L 1/09 |

OTHER PUBLICATIONS

Borde, B. et al: "Thermal properties of isomalt: A diastereomer mixture" Journal of Thermal Analysis and Calorimetry, Kluwer Academic Publishers, DO, vol. 69, No. 1, Jul. 1, 2002 (Jul. 1, 2002), pp. 267-280, XP019254220, ISSN: 1572-8943.

* cited by examiner

ISOMALT-CONTAINING TABLETS AND METHODS FOR THE PRODUCTION THEREOF

CROSS-REFERENCE TO RELATED APPLICATIONS

This application is a 371 U.S. National Stage of International Application No. PCT/EP2009/000712, filed Feb. 4, 2009. This application claims the benefit of German Patent Application No. DE 10 2008 012 015.4, filed Mar. 1, 2008, the disclosures of which are entirely incorporated by reference herein.

FIELD

The present invention relates to improved isomalt-containing compressed products and methods to produce the same.

BACKGROUND

In the development of pharmaceutical dosage forms, extreme attention is paid to the bioavailability of the active ingredients. Compressed products, also known as tablets, are frequently used for administering pharmaceutically active ingredients. To systematically release these active ingredients, in galenics, tablets with different compositions are provided which have a specific dissolution period, thus disintegration time.

Rapidly disintegrating tablets, so-called "oro-dispersible tablets" (ODT), are increasingly gaining in importance in the market. For this dosage form, a disintegration time in the oral cavity of less than 60 seconds, in particular less than 20 seconds is desired without the need of additional fluid intake.

The use of mixtures of 1,6-GPS (6-O-α-D-Glucopyranosyl-D-sorbitol) and 1,1-GPM (1-O-α-D-Glucopyranosyl-D-mannito) for producing tablets is known from DE 196 39 343 A1 and DE 199 43 491 A1.

Isomalt is a mixture of the two stereoisomers 1,6-GPS and 1,1-GPM. Isomalt is also known as Palatinit® or galenIQ®. Isomalt is obtained by hydrogenation of isomaltulose. In pharmacopoeias, isomalt is defined as an at least 98% pure mixture of 1,6-GPS and 1,1-GPM, wherein none of the two components is contained with less than 3% with respect to the dry substance.

Due to the sensory properties of isomalt, suitability for the use in tablets is principally given.

A technical problem underlying the present invention is the provision of isomalt-containing tablets with improved tablet hardness at the same pressing force. In particular, a technical problem underlying the invention is the provision of isomalt-containing tablets with reduced tablet hardness at the same pressing force.

Another technical problem underlying the present invention is the provision of isomalt-containing tablets with improved dissolution period at the same pressing force. In particular, a technical problem underlying the invention is the provision of isomalt-containing tablets with reduced dissolution period at the same pressing force.

Another technical problem underlying the present invention is the provision of methods for controlling the tablet hardness of isomalt-containing tablets. In particular, a technical problem underlying the invention is the provision of methods for reducing the tablet hardness of isomalt-containing tablets.

Another technical problem underlying the invention is the provision of methods for controlling the dissolution period of isomalt-containing tablets. In particular, a technical problem underlying the invention is the provision of methods for reducing the dissolution period of isomalt-containing tablets.

Another technical problem underlying the present invention is the provision of methods for producing isomalt-containing tablets which contain a small portion of magnesium stearate, in particular isomalt-containing tablets which contain no magnesium stearate, and isomalt-containing tablets themselves.

SUMMARY

The invention solves its underlying technical problems by providing methods and tablets according to the claims.

In particular, the invention solves its underlying technical problems by providing a method for producing a tablet, wherein isomalt is mixed with 1,6-GPS (6-O-α-D-Glucopyranosyl-D-sorbitol) and/or with 1,1-GPM (1-O-α-D-Glucopyranosyl-D-mannitol) and the mixture is pressed into a tablet.

In connection with this invention, isomalt is to be understood as a composition of 1,6-GPS and 1,1-GPM.

Preferably, according to the invention, the isomalt contains at least 98% by weight 1,6-GPS and 1,1-GPM. Preferably, according to the invention, the isomalt contains at least 3% by weight 1,6-GPS and at least 3% by weight 1,1-GPM. Preferably, according to the invention, the isomalt contains at least 98% by weight 1,6-GPS and 1,1-GPM and at least 3% by weight 1,6-GPS and at least 3% by weight 1,1-GPM.

Preferably, according to the invention, the isomalt contains 20% by weight to 90% by weight 1,6-GPS. Preferably, according to the invention, the isomalt contains 40% by weight to 85% by weight 1,6-GPS. Preferably, according to the invention, the isomalt contains 43% by weight to 80% by weight 1,6-GPS. Preferably, according to the invention, the isomalt contains 43% by weight to 57% by weight 1,6-GPS. Preferably, according to the invention, the isomalt contains 75% by weight to 80% by weight 1,6-GPS.

Preferably, according to the invention, the isomalt contains 15% by weight to 90% by weight 1,1-GPM. Preferably, according to the invention, the isomalt contains 40% by weight to 85% by weight 1,1-GPM. Preferably, according to the invention, the isomalt contains 43% by weight to 60% by weight 1,1-GPM. Preferably, according to the invention, the isomalt contains 43% by weight to 57% by weight 1,1-GPM. Preferably, according to the invention, the isomalt contains 75% by weight to 80% by weight 1,1-GPM.

Preferably, according to the invention, the isomalt contains 1,6-GPS and 1,1-GPM in a ratio of approximately 1 to 1. Preferably, according to the invention, the isomalt contains 1,6-GPS and 1,1-GPM in a ratio of approximately 3 to 1, particularly preferably in a ratio of 3 to 1.

In the prior art, isomalt is frequently obtained from the hydrogenation, in particular catalytic hydrogenation, of isomaltulose, wherein a nearly equimolar mixture of 1,6-GPS and 1,1-GPM is obtained. The desired ratio of 1,6-GPS and 1,1-GPM in isomalt can then be obtained by methods known to the person skilled in the art, in particular by enrichment methods such as, for example, precipitation or crystallization.

Preferably, according to the invention, the isomalt is obtained from the hydrogenation of isomaltulose. Preferably, according to the invention, the ratio of 1,6-GPS and 1,1-GPM is set between 1 to 99 and 99 to 1, particularly preferably between 3 to 97 and 97 to 3, and more preferably between 1 to 9 and 9 to 1.

Preferably, according to the invention, at least 95% by weight of the isomalt has a grain size of at most 2000 μm, particularly preferably 1000 μm. Preferably, according to the invention, at least 95% by weight of the isomalt has a grain size of at most 500 μm.

Preferably, according to the invention, the isomalt has a grain size of at most 2000 μm, particularly preferably 1000 μm. Preferably, according to the invention, the isomalt has a grain size of at most 750 μm, particularly preferably 600 μm.

Preferably, according to the invention, 10% by weight to 90% by weight of the isomalt has a grain size of at least 150 μm, particularly preferably of at least 200 μm, more preferably of at least 250 μm. Preferably, according to the invention, 35% by weight to 70% by weight of the isomalt has a grain size of at least 150 μm, particularly preferably of at least 200 μm, more preferably of at least 250 μm. Preferably, according to the invention, at least 10% by weight of the isomalt has a grain size of at least 150 μm, particularly preferably of at least 200 μm, more preferably of at least 250 μm. Preferably, according to the invention, at least 20% by weight of the isomalt has a grain size of at least 150 μm, particularly preferably of at least 200 μm, more preferably of at least 250 μm.

Preferably, according to the invention, at least 30% by weight of the isomalt has a grain size of at least 150 μm, particularly preferably of at least 200 μm, more preferably of at least 250 μm. Preferably, according to the invention, at least 35% by weight of the isomalt has a grain size of at least 150 μm, particularly preferably of at least 200 μm, more preferably of at least 250 μm. Preferably, according to the invention, at least 40% by weight of the isomalt has a grain size of at least 150 μm, particularly preferably of at least 200 μm, more preferably of at least 250 μm. Preferably, according to the invention, at most 90% by weight of the isomalt has a grain size of at least 150 μm, particularly preferably of at least 200 μm, more preferably of at least 250 μm. Preferably, according to the invention, at most 80% by weight of the isomalt has a grain size of at least 150 μm, particularly preferably of at least 200 μm, more preferably of at least 250 μm. Preferably, according to the invention, at most 70% by weight of the isomalt has a grain size of at least 150 μm, particularly preferably of at least 200 μm, more preferably of at least 250 μm.

Preferably, according to the invention, at least 80% by weight of the isomalt has a grain size of at least 50 μm, particularly preferably 60 μm. Preferably, according to the invention, at least 80% by weight of the isomalt has a grain size of at least 63 μm.

Preferably, according to the invention, at least 85% by weight of the isomalt has a grain size of at least 50 μm, particularly preferably 60 μm. Preferably, according to the invention, at least 85% of the isomalt has a grain size of at least 63 μm.

Preferably, according to the invention, at least 90% by weight of the isomalt has a grain size of at least 50 μm, particularly preferred 60 μm. Preferably, according to the invention, at least 90% by weight of the isomalt has a grain size of at least 63 μm.

Preferably, according to the invention, the isomalt has a grain size of at least 10 μm, particularly preferred 50 μm. Preferably, according to the invention, the isomalt has a grain size of at most 60 μm, particularly preferred 63 μm.

Preferably, according to the invention, the grain size is determined by sieve measurement, preferably by a mechanical sieve shaker. Preferably, according to the invention, the grain size is determined according to Ph. Eur. 2.9.12 of the European Pharmacopoeia.

Preferably, according to the invention, the isomalt involves agglomerated isomalt. Preferably, according to the invention, the isomalt has been agglomerated prior to the use in the method according to the invention.

Preferably, according to the invention, the isomalt involves non-agglomerated isomalt. Preferably, according to the invention, the isomalt involves galenIQ721®.

The tablet hardness and the dissolution period of tablets depend, among other things, on the nature and extent of the particle deformation during the pressing process. Nature and extent of the particle deformation depend in turn on the mechanical material properties, in particular the modulus of elasticity, the size of the particles, the shape of the particles, for example the crystal form, the isotropy of the particles, for example defects in the crystal structure, and the position with respect to the applied force.

Surprisingly, it was found that tablet hardness and dissolution period of an isomalt-containing tablet change if the isomalt is mixed prior to pressing with additional 1,6-GPS and/or 1,1-GPM. Surprisingly, it was found that the pressing of isomalt with a certain ratio of 1,6-GPS and 1,1-GPM results in a tablet with a different tablet hardness and/or dissolution period than the same pressing with the same pressing force of a mixture of isomalt and 1,6-GPS and/or 1,1-GPM which overall has the same ratio of 1,6-GPS and 1,1-GPM. In particular, it was surprisingly found that for an isomalt-containing tablet, the tablet hardness can be reduced and the dissolution period can be shortened by mixing the isomalt with 1,6-GPs and/or 1,1-GPM prior to the pressing. Without being bound by the theory, the different structure of the 1,6-GPS and 1,1-GPM contained in the isomalt and the additional 1,6-GPS and/or 1,1-GPM could be responsible for the change of the tablet hardness and the dissolution period. For example, the existence of tomahawk structures in the additionally mixed 1,6-GPS and/or 1,1-GPM could result in a changed overall structure in the tablet. Also, a different distribution of the crystals could influence the tablet hardness and the dissolution period. Without being bound by the theory, isomalt could be present in the form of mosaic crystal structures while the added 1,6-GPS and/or 1,1-GPM do not have a mosaic crystal structure. In this way, tablets which have been produced according to the invention and with comparable grain size could differ in terms of their specific surface from isomalt tablets from the prior art.

Also, the different crystal structures in the tablets could result in differences in the microstructural constitution, in particular in different pore diameters and/or pore size distributions.

In connection with the present invention, a compressed product is to be understood as a tablet which is produced from powders and/or granules by applying pressing power. The compressed tablet has a certain tablet hardness.

The tablet hardness can be determined, for example, according to the method according to Ph. Eur. 2.9.8 of the European Pharmacopoeia. For example, as a measuring principle, a load cell with strain gauges can be used. For example, as measuring device, a device TBH 30 from Erweka can be used.

Pressing with a certain pressure power is known to the person skilled in the art. The pressing can be carried out with methods known from the prior art.

Preferably, according to the invention, the mixture of isomalt and 1,6-GPS and/or 1,1-GPM is directly pressed. Preferably, according to the invention, the mixture of isomalt and 1,6-GPS is directly pressed. Preferably, according to the invention, the mixture of isomalt and 1,1-GPM is directly pressed.

Preferably, according to the invention, the pressing is carried out with a force of 1.0 to 15.0 kN. Preferably, according to the invention, the pressing is carried out with a force of 2.0 to 12.0 kN. Preferably, according to the invention, the pressing is carried out with a force of 2.0 to 10.0 kN. Preferably, according to the invention, the pressing is carried out with a force of 2.0 to 8.0 kN. Preferably, according to the invention, the pressing is carried out with a force of at least 1.0 kN. Preferably, according to the invention, the pressing is carried out with a force of at least 2.0 kN. Preferably, according to the invention, the pressing is carried out with a force of at least 3.0 kN. Preferably, according to the invention, the pressing is carried out with a force of at least 4.0 kN. Preferably, according to the invention, the pressing is carried out with a force of at most 20.0 kN. Preferably, according to the invention, the pressing is carried out with a force of at most 15.0 kN. Preferably, according to the invention, the pressing is carried out with a force of at most 12.0 kN. Preferably, according to the invention, the pressing is carried out with a force of at most 10.0 kN. Preferably, according to the invention, the pressing is carried out with a force of at most 8.0 kN.

In connection with the present invention, the 1,6-GPS and the 1,1-GPM which are mixed with the isomalt are to be understood as such 1,6-GPS and 1,1-GPM which are not contained in the used isomalt prior to mixing. Thus, the 1,6-GPS and the 1,1-GPM which are mixed with the isomalt do not involve the 1,6-GPS and 1,1-GPM contained in the isomalt fraction. Thus, according to the invention, the 1,6-GPS and 1,1-GPM present in the form of isomalt are mixed with additional 1,6-GPS and/or additional 1,1-GPM.

Preferably, according to the invention, the 1,6-GPS and/or 1,1-GPM is physically mixed with the isomalt. The mixing can be carried out, for example, by means of a diffusion mixer.

Preferably, according to the invention, the 1,6-GPS and/or 1,1-GPM mixed with the isomalt are not agglomerated with the isomalt.

Preferably, according to the invention, isomalt is mixed with 1,6-GPS and the mixture is pressed into a tablet. Preferably, according to the invention, isomalt is mixed with 1,1-GPM and the mixture is pressed into a tablet.

Preferably, according to the invention, the ratio between isomalt and 1,6-GPS and/or 1,1 GPM is 1:99 to 99:1. Preferably, according to the invention, the ratio between isomalt and 1,6-GPS and/or 1,1 GPM is 1:9 to 9:1. Preferably, according to the invention, the ratio between isomalt and 1,6-GPS and/or 1,1 GPM is 2:8 to 8:2. Preferably, according to the invention, the ratio between isomalt and 1,6-GPS and/or 1,1 GPM is 3:7 to 7:3. Preferably, according to the invention, the ratio between isomalt and 1,6-GPS and/or 1,1 GPM is 4:6 to 6:4. Preferably, according to the invention, the ratio between isomalt and 1,6-GPS and/or 1,1 GPM is 1:1 to 7:3. Preferably, according to the invention, the ratio between isomalt and 1,6-GPS and/or 1,1 GPM is 1:1 to 6:4. Preferably, according to the invention, the ratio between isomalt and 1,6-GPS and/or 1,1 GPM is 1:1 to 4:1. Preferably, according to the invention, the ratio between isomalt and 1,6-GPS and/or 1,1 GPM is 1:1 to 9:1. Preferably, according to the invention, the ratio between isomalt and 1,6-GPS and/or 1,1 GPM is 1:1. Preferably, according to the invention, the ratio between isomalt and 1,6-GPS and/or 1,1 GPM is 7:3.

Preferably, according to the invention, the ratio between isomalt and 1,6-GPS is 1:99 to 99:1. Preferably, according to the invention, the ratio between isomalt and 1,6-GPS is 1:9 to 9:1. Preferably, according to the invention, the ratio between isomalt and 1,6-GPS is 2:8 to 8:2. Preferably, according to the invention, the ratio between isomalt and 1,6-GPS is 3:7 to 7:3. Preferably, according to the invention, the ratio between isomalt and 1,6-GPS is 4:6 to 6:4. Preferably, according to the invention, the ratio between isomalt and 1,6-GPS is 1:1 to 7:3. Preferably, according to the invention, the ratio between isomalt and 1,6-GPS is 1:1 to 6:4. Preferably, according to the invention, the ratio between isomalt and 1,6-GPS is 1:1 to 4:1. Preferably, according to the invention, the ratio between isomalt and 1,6-GPS is 1:1 to 9:1. Preferably, according to the invention, the ratio between isomalt and 1,6-GPS is 1:1. Preferably, according to the invention, the ratio between isomalt and 1,6-GPS is 7:3.

Preferably, according to the invention, the ratio between isomalt and 1,1-GPM is 1:99 to 99:1. Preferably, according to the invention, the ratio between isomalt and 1,1-GPM is 1:9 to 9:1. Preferably, according to the invention, the ratio between isomalt and 1,1-GPM is 2:8 to 8:2. Preferably, according to the invention, the ratio between isomalt and 1,1-GPM is 3:7 to 7:3. Preferably, according to the invention, the ratio between isomalt and 1,1-GPM is 4:6 to 6:4. Preferably, according to the invention, the ratio between isomalt and 1,1-GPM is 1:1 to 7:3. Preferably, according to the invention, the ratio between isomalt and 1,1-GPM is 1:1 to 6:4. Preferably, according to the invention, the ratio between isomalt and 1,1-GPM is 1:1 to 4:1. Preferably, according to the invention, the ratio between isomalt and 1,1-GPM is 1:1 to 9:1. Preferably, according to the invention, the ratio between isomalt and 1,1-GPM is 1:1. Preferably, according to the invention, the ratio between isomalt and 1,1-GPM is 7:3.

Preferably, according to the invention, the 1,6-GPS and/or the 1,1-GPM are ground prior to mixing with the isomalt. Preferably, according to the invention, the 1,6-GPS is ground prior to mixing with the isomalt. Preferably, according to the invention, the 1,1-GPM is ground prior to mixing with the isomalt.

Preferably, according to the invention, the 1,6-GPS and/or the 1,1-GPM are sieved prior to mixing with the isomalt. Preferably, according to the invention, the 1,6-GPS is sieved prior to mixing with the isomalt. Preferably, according to the invention, the 1,1-GPM is sieved prior to mixing with the isomalt.

Preferably, according to the invention, the 1,6-GPS and/or the 1,1-GPM are not agglomerated prior to mixing with the isomalt. Preferably, according to the invention, the 1,6-GPS is not agglomerated prior to mixing with the isomalt. Preferably, according to the invention, the 1,1-GPM is not agglomerated prior to mixing with the isomalt.

Preferably, according to the invention, the 1,6-GPS and/or the 1,1-GPM have a tomahawk structure prior to mixing with the isomalt. Preferably, according to the invention, the 1,6-GPS has a tomahawk structure prior to mixing with the isomalt. Preferably, according to the invention, the 1,1-GPM has a tomahawk structure prior to mixing with the isomalt.

Preferably, according to the invention, the 1,6-GPS and/or the 1,1-GPM have a particle size of at most 500 µm prior to mixing with the isomalt. Preferably, according to the invention, the 1,6-GPS and/or the 1,1-GPM have a particle size of at most 250 µm prior to mixing with the isomalt. Preferably, according to the invention, the 1,6-GPS and/or the 1,1-GPM have a particle size of at most 150 µm prior to mixing with the isomalt. Preferably, according to the invention, the 1,6-GPS and/or the 1,1-GPM have a particle size of at most 100 µm prior to mixing with the isomalt. Preferably, according to the invention, the 1,6-GPS and/or the 1,1-GPM have a particle size of 40 µm to 150 µm prior to mixing with the isomalt. Preferably, according to the invention, the 1,6-GPS and/or the 1,1-GPM have a particle size of 50 µm to 100 µm prior to mixing with the isomalt. Preferably, according to the invention, the 1,6-GPS and/or the 1,1-GPM have a particle size of 63 µm to 90 µm prior to mixing with the isomalt. Preferably, according to the invention, the 1,6-GPS and/or the 1,1-GPM have a particle size of at least 0.2 µm prior to mixing with the isomalt. Preferably, according to the invention, the 1,6-GPS and/or the 1,1-GPM have a particle size of at least 1 µm prior to mixing with the isomalt. Preferably, according to the invention, the 1,6-GPS and/or the 1,1-GPM have a particle size of at least 10 µm prior to mixing with the isomalt. Preferably, according to the invention, the 1,6-GPS and/or the 1,1-GPM have a particle size of at least 20 µm prior to mixing with the isomalt. Preferably, according to the invention, the 1,6-GPS and/or the 1,1-GPM have a particle size of at least 30 µm prior to mixing with the isomalt.

Preferably, according to the invention, the 1,6-GPS and/or the 1,1-GPM have a particle size of at least 40 µm prior to mixing with the isomalt. Preferably, according to the invention, the 1,6-GPS and/or the 1,1-GPM have a particle size of at least 50 µm prior to mixing with the isomalt. Preferably, according to the invention, the 1,6-GPS and/or the 1,1-GPM have a particle size of at least 60 µm prior to mixing with the isomalt. Preferably, according to the invention, the 1,6-GPS and/or the 1,1-GPM have a particle size of at least 63 µm prior to mixing with the isomalt.

Preferably, according to the invention, the 1,6-GPS has a particle size of at most 500 µm prior to mixing with the isomalt. Preferably, according to the invention, the 1,6-GPS has a particle size of at most 250 µm prior to mixing with the isomalt. Preferably, according to the invention, the 1,6-GPS has a particle size of at most 150 µm prior to mixing with the isomalt. Preferably, according to the invention, the 1,6-GPS has a particle size of at most 100 µm prior to mixing with the isomalt. Preferably, according to the invention, the 1,6-GPS has a particle size of 40 µm to 150 µm prior to mixing with the isomalt. Preferably, according to the invention, the 1,6-GPS has a particle size of 50 µm to 100 µm prior to mixing with the isomalt. Preferably, according to the invention, the 1,6-GPS has a particle size of 63 µm to 90 µm prior to mixing with the isomalt. Preferably, according to the invention, the 1,6-GPS has a particle size of at least 0.2 µm prior to mixing with the isomalt. Preferably, according to the invention, the 1,6-GPS has a particle size of at least 1 µm prior to mixing with the isomalt. Preferably, according to the invention, the 1,6-GPS has a particle size of at least 10 µm prior to mixing with the isomalt. Preferably, according to the invention, the 1,6-GPS has a particle size of at least 20 µm prior to mixing with the isomalt. Preferably, according to the invention, the 1,6-GPS has a particle size of at least 30 µm prior to mixing with the isomalt. Preferably, according to the invention, the 1,6-GPS has a particle size of at least 40 µm prior to mixing with the isomalt. Preferably, according to the invention, the 1,6-GPS has a particle size of at least 50 µm prior to mixing with the isomalt. Preferably, according to the invention, the 1,6-GPS has a particle size of at least 60 µm prior to mixing with the isomalt. Preferably, according to the invention, the 1,6-GPS has a particle size of at least 63 µm prior to mixing with the isomalt.

Preferably, according to the invention, the 1,1-GPM has a particle size of at most 500 µm prior to mixing with the isomalt. Preferably, according to the invention, the 1,1-GPM has a particle size of at most 250 µm prior to mixing with the isomalt. Preferably, according to the invention, the 1,1-GPM has a particle size of at most 150 µm prior to mixing with the isomalt. Preferably, according to the invention, the 1,1-GPM has a particle size of at most 100 µm prior to mixing with the isomalt. Preferably, according to the invention, the 1,1-GPM has a particle size of 40 µm to 150 µm prior to mixing with the isomalt. Preferably, according to the invention, the 1,1-GPM has a particle size of 50 µm to 100 µm prior to mixing with the isomalt. Preferably, according to the invention, the 1,1-GPM has a particle size of 63 µm to 90 µm prior to mixing with the isomalt. Preferably, according to the invention, the 1,1-GPM has a particle size of at least 0.2 µm prior to mixing with the isomalt. Preferably, according to the invention, the 1,1-GPM has a particle size of at least 1 µm prior to mixing with the isomalt. Preferably, according to the invention, the 1,1-GPM has a particle size of at least 10 µm prior to mixing with the isomalt. Preferably, according to the invention, the 1,1-GPM has a particle size of at least 20 µm prior to mixing with the isomalt. Preferably, according to the invention, the 1,1-GPM has a particle size of at least 30 µm prior to mixing with the isomalt. Preferably, according to the invention, the 1,1-GPM has a particle size of at least 40 µm prior to mixing with the isomalt. Preferably, according to the invention, the 1,1-GPM has a particle size of at least 50 µm prior to mixing with the isomalt. Preferably, according to the invention, the 1,1-GPM has a particle size of at least 60 µm prior to mixing with the isomalt. Preferably, according to the invention, the 1,1-GPM has a particle size of at least 63 µm prior to mixing with the isomalt.

Preferably, according to the invention, the 1,6-GPS and/or 1,1-GPM have a purity prior to mixing with the isomalt of at least 90% by weight, preferably 98% by weight, particularly preferably 99% by weight. Preferably, according to the invention, the 1,6-GPS and/or 1,1-GPM have a purity prior to mixing with the isomalt of at least 90% by weight. Preferably, according to the invention, the 1,6-GPS and/or 1,1-GPM have a purity prior to mixing with the isomalt of at least 98% by weight. Preferably, according to the invention, the 1,6-GPS and/or 1,1-GPM have a purity prior to mixing with the isomalt of at least 99% by weight.

Preferably, according to the invention, the 1,6-GPS has a purity prior to mixing with the isomalt of at least 90% by weight, preferably 98% by weight, particularly preferably 99% by weight. Preferably, according to the invention, the 1,6-GPS has a purity prior to mixing with the isomalt of at least 90% by weight. Preferably, according to the invention, the 1,6-GPS has a purity prior to mixing with the isomalt of at least 98% by weight. Preferably, according to the invention, the 1,6-GPS has a purity prior to mixing with the isomalt of at least 99% by weight.

Preferably, according to the invention, the 1,1-GPM has a purity prior to mixing with the isomalt of at least 90% by weight, preferably 98% by weight, particularly preferably 99% by weight. Preferably, according to the invention, the 1,1-GPM has a purity prior to mixing with the isomalt of at least 90% by weight. Preferably, according to the invention, the 1,1-GPM has a purity prior to mixing with the isomalt of at least 98% by weight. Preferably, according to the invention, the 1,1-GPM has a purity prior to mixing with the isomalt of at least 99% by weight.

Preferably, according to the invention, the mixture contains in addition at least one pharmaceutically active ingredient. In connection with the present invention, pharmaceutically active ingredients are to be understood as substances which have a desired prophylactic or therapeutic effect on the human or animal body. These substances thus serve in particular for the prophylaxis and the therapy of deficiencies or illnesses. Preferably, according to the invention, enzymes, coenzymes, mineral nutrients, vitamins, antibiotics, microbicidal or fungicidal substances, or other pharmaceutical substances are contained in the mixture.

Preferably, according to the invention, the mixture contains at least one flow agent. Preferably, according to the invention, the flow agent portion of the mixture is 0.1 to 0.3% by weight. Preferably, according to the invention, the at least one flow agent is $SiO_2$. Preferably, according to the invention, the at least one flow agent is $Ca_3PO_4$. Preferably, according to the invention, the mixture contains in addition at least one binding agent. Preferably, according to the invention, the mixture contains in addition at least one lubricant. Preferably, according to the invention, the mixture does not contain a flow agent. Preferably, according to the invention, the mixture does not contain a binding agent. Preferably, according to the invention, the mixture does not contain a lubricant.

Preferably, according to the invention, the mixture contains in addition magnesium stearate. Preferably, according to the invention, the mixture contains less magnesium stearate than a mixture for producing a comparable tablet from the prior art. Preferably, according to the invention, the mixture does not contain magnesium stearate.

Preferably, according to the invention, the mixture contains in addition a substance from the group consisting of flavoring agents, colorants, disintegrants, an intensive sweetener, monosaccharides, disaccharides, monosaccharide alcohols, disaccharide alcohols, starch, starch derivates, cellulose, cellulose derivates, inulin, or mixtures thereof. Preferably, according to the invention, the mixture contains in addition at least one flavoring agent. Preferably, according to the invention, the mixture contains in addition at least one colorant. Preferably, according to the invention, the mixture contains in addition at least one disintegrant. Preferably, according to the invention, the mixture contains in addition at least one intensive sweetener. Preferably, according to the invention, the mixture contains in addition at least one monosaccharide. Preferably, according to the invention, the mixture contains in addition at least one disaccharide. Preferably, according to the invention, the mixture contains in addition at least one monosaccharide alcohol. Preferably, according to the invention, the mixture contains in addition at least one disaccharide alcohol. Preferably, according to the invention, the mixture contains in addition at least one substance from the group consisting of starch, starch derivates, cellulose, cellulose derivates, inulin, or mixtures thereof.

Preferably, according to the invention, the mixture does not contain disintegrants.

Preferably, according to the invention, the mixture does not contain sugar. Preferably, according to the invention, the mixture does not contain saccharose. Preferably, according to the invention, the mixture does not contain glucose. Preferably, according to the invention, the mixture does not contain fructose.

The invention also relates to a tablet containing a) isomalt and, in addition, b) 1,6-GPS (6-O-α-D-Glucopyranosyl-sorbitol) and/or 1,1-GPM (1-O-α-D-Glucopyranosyl-D-mannitol).

Preferably, according to the invention, the isomalt involves an isomalt as described above. Preferably, according to the invention, the 1,6-GPS involves a 1,6-GPS as described above. Preferably, according to the invention, the 1,1-GPM involves a 1,1-GPM as described above.

Preferably, according to the invention, the tablet contains a mixture as described above. Preferably, according to the invention, the tablet consists of a mixture as described above.

Preferably, according to the invention, the tablet contains a) isomalt and, in addition, b) 1,6-GPS. Preferably, according to the invention, the tablet contains a) isomalt and, in addition, b) 1,1-GPM.

Preferably, according to the invention, the tablet contains, in addition, a pharmaceutically active ingredient.

Preferably, according to the invention, the tablet is a directly pressed tablet.

Preferably, according to the invention, the tablet does not contain magnesium stearate.

Preferably, according to the invention, the tablet does not contain disintegrants.

Preferably, according to the invention, the tablet does not contain sugar. Preferably, according to the invention, the tablet does not contain saccharose. Preferably, according to the invention, the tablet does not contain glucose. Preferably, according to the invention, the tablet does not contain fructose.

Preferably, according to the invention, the tablet is the core of a dragee.

Preferably, according to the invention, the tablet is not covered with an enveloping layer. Preferably, according to the invention, the tablet is covered with an enveloping layer.

Preferably, according to the invention, the tablet is produced according to a method according to the invention.

Preferably, according to the invention, the tablet has a short dissolution period. Preferably, according to the invention, the tablet has a shorter dissolution period than a comparable tablet from the prior art. Preferably, according to the invention, the tablet has a dissolution period of 500 seconds to 5 seconds. Preferably, according to the invention, the tablet has a dissolution period of 200 seconds to 10 seconds. Preferably, according to the invention, the tablet has a dissolution period of less than 200 seconds. Preferably, according to the invention, the tablet has a dissolution period of less than 100 seconds. Preferably, according to the invention, the tablet has a dissolution period of less than 60 seconds.

In connection with the present invention, dissolution period of the tablet is to be understood as the disintegration time. The dissolution period can be determined, for example, according to the method for determining the disintegration time according to Ph. Eur. 2.9.1 of the European Pharmacopoeia.

A person skilled in the art knows the dissolution period suitable for his purposes.

The invention also relates to a mixture of isomalt and 1,6-GPS and/or 1,1-GPM. Particularly preferred embodiments of a mixture according to the invention and its components are described above.

The invention also relates to the use of a mixture for producing a tablet.

Further advantageous configurations of the invention are to be found in the sub-claims.

DRAWINGS

The following examples and the figures illustrate the invention in detail.

FIG. 1 shows the ratio of pressing force to tablet hardness (measured as tablet breaking force) of tablets according to the invention which were produced with different pressing forces from a mixture of isomalt and 1,6-GPS, and of comparable tablets which were produced from an isomalt mixture without the addition of 1,6-GPS. The tablets according to the invention and the comparative tablets contain 1,6-GPS and 1,1-GPM in the same proportion of 3:1.

Figure 2:
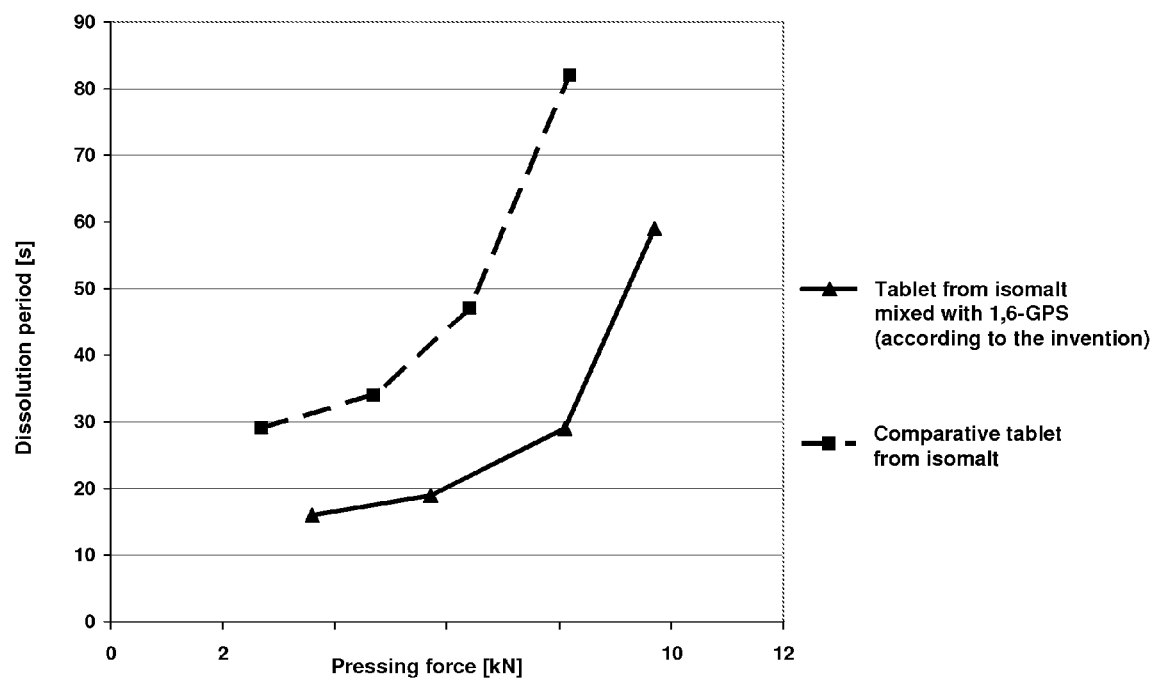

FIG. 2 shows the ratio of pressing force to dissolution period of tablets according to the invention which were produced with different pressing forces from a mixture of isomalt and 1,6-GPS, and of comparable tablets which were produced from an isomalt mixture without the addition of 1,6-GPS. The tablets according to the invention and the comparative tablets contain 1,6-GPS and 1,1-GPM in the same proportion of 3:1.

Figure 3:
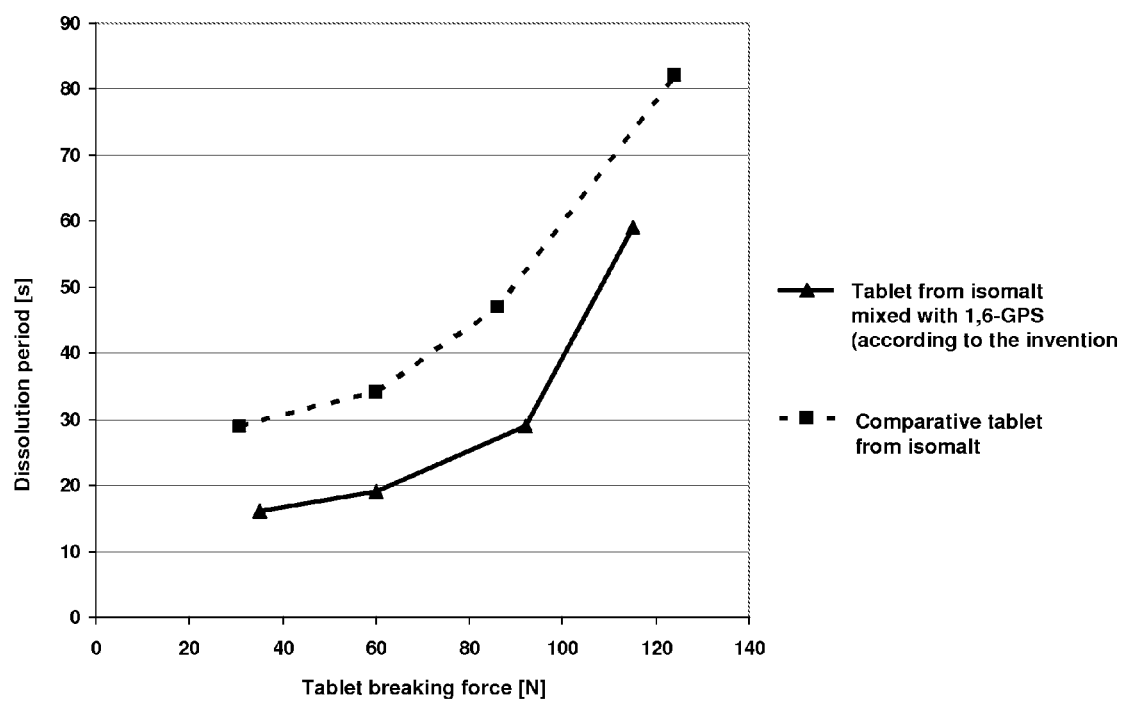

FIG. 3 shows the ratio of tablet hardness (measured as tablet breaking force) to dissolution period of tablets according to the invention which were produced with different pressing forces from a mixture of isomalt and 1,6-GPS, and of comparable tablets which were produced from an isomalt mixture without the addition of 1,6-GPS. The tablets according to the invention and the comparative tablets contain 1,6-GPS and 1,1-GPM in the same proportion of 3:1.

DETAILED DESCRIPTION

EXAMPLES

Example 1

Production of Tablets According to the Invention from Isomalt and 1,6-GPS 1,6-GPS was ground in such a manner that 5% by weight of the 1,6-GPS had a particle size of at least 125.98 μm, 50% by weight of the 1,6-GPS had a particle size of at least 42.18 μm, and 95% by weight of the 1,6-GPS had a particle size of at least 4.11 μm. After that, the 1,6-GPS was sieved so that the entire 1,6-GPS was smaller than 100 μm.

As isomalt, two different isomalt grades were used.

Grade A contained 53.55% by weight 1,6-GPS and 45.69% by weight 1,1-GPM. 11.8% by weight had a grain size smaller than 63 μm. 88.12% by weight had a grain size of 63 μm to 500 μm. 0.08% by weight had a grain size greater than 500 μm.

Grade B contained 75.93% by weight 1,6-GPS and 22.63% by weight 1,1-GPM. 8.34% by weight had a grain size smaller than 63 μm. 91,52% by weight had a grain size of 63 μm to 500 μm. 0.14% by weight had a grain size greater than 500 μm.

The two isomalt grades were each mixed with 10% by weight, 30% by weight, 50% by weight, and 90% by weight (with respect to the total quantity of isomalt and additional 1,6-GPS) of 1,6-GPS in a diffusion mixer.

From the mixture, tablets with a target weight of 600 mg and a target diameter of 12 mm were directly pressed with a press of the type FETTE P1200 IG. Here, different pressing forces were applied so that tablets with a tablet hardness of approximately 30 N, 60 N, 90 N, or 120 N were produced. Of each tablet grade, at least 16 tablets were produced.

Example 2

Production of Tablets According to the Invention from Isomalt and 1,1-GPM 1,1-GPM was ground in such a manner that 5% by weight of the 1,1-GPM had a particle size of at least 67.48 μm, 50% by weight of 1,1-GPM had a particle size of at least 17.71 μm, and 95% by weight of the 1,1-GPM had a particle size of at least 1.11 μm. After that, the 1,1-GPM was sieved so that the entire 1,1-GPM was smaller than 100 μm.

As isomalt, the two different isomalt grades of example 1 were used.

The two isomalt grades were each mixed with 10% by weight, 30% by weight, 50% by weight, and 90% by weight (with respect to the total quantity of isomalt and additional 1,1-GPM) 1,1-GPS as in example 1.

From the mixture, tablets with a target weight of 600 mg and a target diameter of 12 mm were directly pressed with a press of the type FETTE P1200 IG. Here, different pressing forces were applied so that tablets with a tablet hardness of approximately 30 N, 60 N, 90 N, or 120 N were produced. Of each tablet grade, at least 16 tablets were produced.

Example 3

Measurement of the Breaking Force

For measuring the breaking force, the tablet hardness was determined according to the method described in PH. Eur. under 2.9.8. The measurement was carried out with the measuring device TBH 30 from Erweka.

The breaking force of each of four tablets according to the invention according to example 1 from the isomalt grade A and 50% by weight 1,6-GPS, and of each of four tablets from a 1,6-GPS-enriched isomalt mixture without the addition of 1,6-GPS was measured. The tablets according to the invention contained 1,6-GPS and 1,1-GPM in the same proportion.

The comparison of the breaking force of the tablets according to the invention and the comparative tablets is shown in FIG. 1.

Example 4

Measurement of the Dissolution Period

The dissolution period was measured with a disintegration time tester.

The dissolution period of each of four tablets according to the invention according to example 1 from the isomalt grade A and 50% by weight 1,6-GPS, and of each of four tablets from a 1,6-GPS-enriched isomalt mixture without the addition of 1,6-GPS was measured. The tablets according to the invention contained 1,6-GPS and 1,1-GPM in the same proportion.

The comparison of the dissolution period of the tablets according to the invention and the comparative tablets is shown in FIG. 2.

FIG. 3 shows, at equal hardness, a shorter dissolution period of the tablets according to the invention in comparison to pure isomalt tablets with equal portions of 1,6-GPS and 1,1-GPM.

Example 5

Crystal Structure Images with Scanning Electron Microscope

In a comparison of scanning electron microscope (SEM) images of the fracture surfaces of tablets according to the invention and fracture surfaces of comparative tablets, the tablets according to the invention show a more open-pored microstructure with a higher number of pores.

What is claimed is:

1. A method for producing a tablet, the method comprising:
mixing isomalt comprising a 6-O-α-D-Glucopyranosyl-D-sorbitol (1,6-GPS):1-O-α-D-Glucopyranosyl-D-mannitol (1,1-GPM) ratio of about 1.2:1 with additional 1,6-GPS or with additional 1,1-GPM to form a mixture containing 50% of either the additional 1,6-GPS or the additional 1,1-GPM by weight, with respect to the total quantity of isomalt and the additional 1,6-GPS or the additional 1,1-GPM in the mixture, wherein the additional 1,6-GPS or the additional 1,1-GPM is not contained in the isomalt prior to the mixing, and
directly pressing the mixture with a force of from 2 kN to 15 kN into a tablet having a hardness of from 30 N to 120 N.

2. The method according to claim 1, wherein isomalt is mixed with the additional 1,6-GPS.

3. The method according to claim 1, wherein isomalt is mixed with the additional 1,1-GPM.

4. The method according to claim 1, wherein the additional 1,6-GPS or the additional 1,1-GPM are ground prior to mixing with the isomalt.

5. The method according to claim 1, wherein the additional 1,6-GPS or the additional 1,1-GPM are sieved prior to mixing with the isomalt.

6. The method according to claim 1, wherein the additional 1,6-GPS or the additional 1,1-GPM has a particle size of at most 250 μm prior to mixing with the isomalt.

7. The method according to claim 1, wherein the additional 1,6-GPS or the additional 1,1-GPM has a particle size of at most 100 μm prior to mixing with the isomalt.

8. The method according to claim 1, wherein the additional 1,6-GPS or the additional 1,1-GPM has a particle size of 63 μm to 90 μm prior to mixing with the isomalt.

9. The method according to claim 1, wherein the additional 1,6-GPS or the additional 1,1-GPM has a purity prior to mixing with the isomalt of at least 90% by weight.

10. The method according to claim 1, wherein the mixture contains in addition at least one pharmaceutically active ingredient.

11. The method according to claim 1, wherein the mixture contains in addition a substance from the group consisting of flavoring agents, colorants, disintegrants, starch, starch derivates, cellulose, cellulose derivates, inulin, or mixtures thereof.

12. A tablet comprising a mixture of:
a) isomalt comprising a 6-O-α-D-Glucopyranosyl-D-sorbitol (1,6-GPS):1-O-α-D-Glucopyranosyl-D-mannitol (1,1-GPM) ratio of about 1.2:1; and
b) additional 1,6-GPS or additional 1,1-GPM,
wherein the mixture contains 50% of either the additional 1,6-GPS or the additional 1,1-GPM by weight, with respect to the total quantity of isomalt and the additional 1,6-GPS or the additional 1,1-GPM in the mixture, the additional 1,6-GPS and/or 1,1-GPM are not contained in the isomalt prior to being mixed with the isomalt and are not agglomerated prior to being mixed with the isomalt, and the mixture of isomalt and 1,6-GPS or 1,1-GPM is pressed directly with a force of from 2 kN to 15 kN after mixing to form the tablet, wherein the tablet has a hardness of from 30 N to 120 N.

13. The tablet according to claim 12 comprising:
isomalt and the additional 1,6-GPS.

14. The tablet according to claim 12 comprising:
isomalt and the additional 1,1-GPM.

15. The tablet according to claim 12, wherein the tablet further includes a pharmaceutically active ingredient.

16. A method for producing a tablet, the method comprising:
forming a mixture of isomalt comprising a 6-O-α-D-Glucopyranosyl-D-sorbitol (1,6-GPS):1-O-α-D-Glucopyranosyl-D-mannitol (1,1-GPM) ratio of about 1.2:1, additional 1,6-GPS that is not contained in the isomalt, and additional 1,1-GPM that is not contained in the isomalt, the mixture containing 50% of the additional 1,6-GPS and the additional 1,1-GPM by weight, with respect to the total quantity of isomalt and the additional 1,6-GPS and the additional 1,1-GPM in the mixture; and
directly pressing the mixture with a force of from 2 kN to 15 kN into a tablet having a hardness of from 30 N to 120 N.

17. A method for producing a tablet, the method comprising:
adding either additional 6-O-α-D-Glucopyranosyl-D-sorbitol (1,6-GPS) or additional 1-O-α-D-Glucopyranosyl-D-mannitol (1,1-GPM), a pharmaceutically active ingredient, and at least one optional component selected from the group consisting of flavoring agents, colorants, disintegrants, starch, starch derivates, cellulose, cellulose derivates, inulin, flow agents, magnesium stearate, and combinations thereof to isomalt comprising a 1,6-GPS:1,1-GPM ratio of about 1.2:1 to generate a composition, wherein the composition contains 50% of either the additional 1,6-GPS or the additional 1,1-GPM by weight, with respect to the total weight of the composition, and the additional 1,6-GPS or additional 1,1-GPM are not contained in the isomalt prior to the adding;
mixing the composition to form a mixture consisting of the additional 1,6-GPS or additional 1,1-GPM, the pharmaceutically active ingredient, the isomalt, and the at least one optional component when present; and
directly pressing the mixture with a force of from 2 kN to 15 kN into a tablet having a hardness of from 30 N to 120 N.

18. The method according to claim 17, wherein pressing includes applying a pressing force of from about 4 kN to about 10 kN to the mixture.

19. The method according to claim 1, wherein, prior to mixing, the additional 1,6-GPS or the additional 1,1-GPM has a particle size of at most 500 μm and the isomalt has a grain size of at most 2000 μm.

20. The method according to claim 1, wherein the additional 1,6-GPS or the additional 1,1-GPM has a purity prior to mixing with the isomalt of at least 98% by weight.

21. The method according to claim 1, wherein the additional 1,6-GPS or the additonal 1,1-GPM has a purity prior to mixing with the isomalt of at least 99% by weight.

* * * * *